United States Patent [19]

Stevens et al.

[11] Patent Number: 4,548,686
[45] Date of Patent: Oct. 22, 1985

[54] SELECTIVE PHOTOCHLORINATION OF 1,1-DICHLOROETHANE

[75] Inventors: James C. Stevens; Donald J. Perettie, both of Midland, Mich.

[73] Assignee: The Dow Chemical Company, Midland, Mich.

[21] Appl. No.: 571,969

[22] Filed: Jan. 18, 1984

Related U.S. Application Data

[63] Continuation of Ser. No. 499,088, May 27, 1983, abandoned, which is a continuation-in-part of Ser. No. 386,148, Jun. 7, 1982, abandoned.

[51] Int. Cl.$^4$ .............................................. B01J 19/12
[52] U.S. Cl. ........................ 204/158 HA; 204/163 R
[58] Field of Search ................... 204/158 HA, 163 R

[56] References Cited

U.S. PATENT DOCUMENTS

| | | | |
|---|---|---|---|
| 2,446,430 | 8/1948 | Norton | 204/163 R |
| 3,019,175 | 1/1962 | Haefner et al. | 204/163 R |
| 3,537,968 | 11/1970 | Chamberlain et al. | 204/163 R |
| 3,580,831 | 5/1971 | Mintz | 204/163 R |
| 3,745,103 | 7/1973 | Richtzenhain et al. | 570/253 |
| 3,948,741 | 4/1976 | McCoy | 204/163 R |
| 4,046,656 | 9/1977 | Davis et al. | 204/158 HA |
| 4,192,823 | 3/1980 | Rideout et al. | 570/253 |
| 4,301,314 | 11/1981 | Rideout et al. | 570/253 |

FOREIGN PATENT DOCUMENTS

| | | | |
|---|---|---|---|
| 2161725 | 7/1972 | Fed. Rep. of Germany . | |
| 3011689 | 4/1980 | Fed. Rep. of Germany | 570/253 |
| 55-079329 | 6/1980 | Japan . | |
| 1337796 | 11/1973 | United Kingdom | 570/253 |

OTHER PUBLICATIONS

Tiffany et al., Science, 157, (Jul., 1967), pp. 41–43.
Seery et al., Journal of Physical Chemistry, vol. 68, No. 8, pp. 2263–2266 (1980).

Primary Examiner—Howard S. Williams
Attorney, Agent, or Firm—Norman L. Sims

[57] ABSTRACT

The invention is a selective process for preparing 1,1,1-trichloroethane comprising irradiating a vaporous mixture comprising 1,1-dichloroethane, chlorine and an effective amount of a photocatalyst wherein the photocatalyst is bromine, a compound which liberates bromine in the presence of chlorine, carbon monoxide, nitric oxide or oxygen, with radiation capable of inducing the selective formation of 1,1,1-trichloroethane. Radiation in the wavelength of between about 250 and 550 nanometers is capable of inducing the selective formation of 1,1,1-trichloroethane.

14 Claims, 1 Drawing Figure

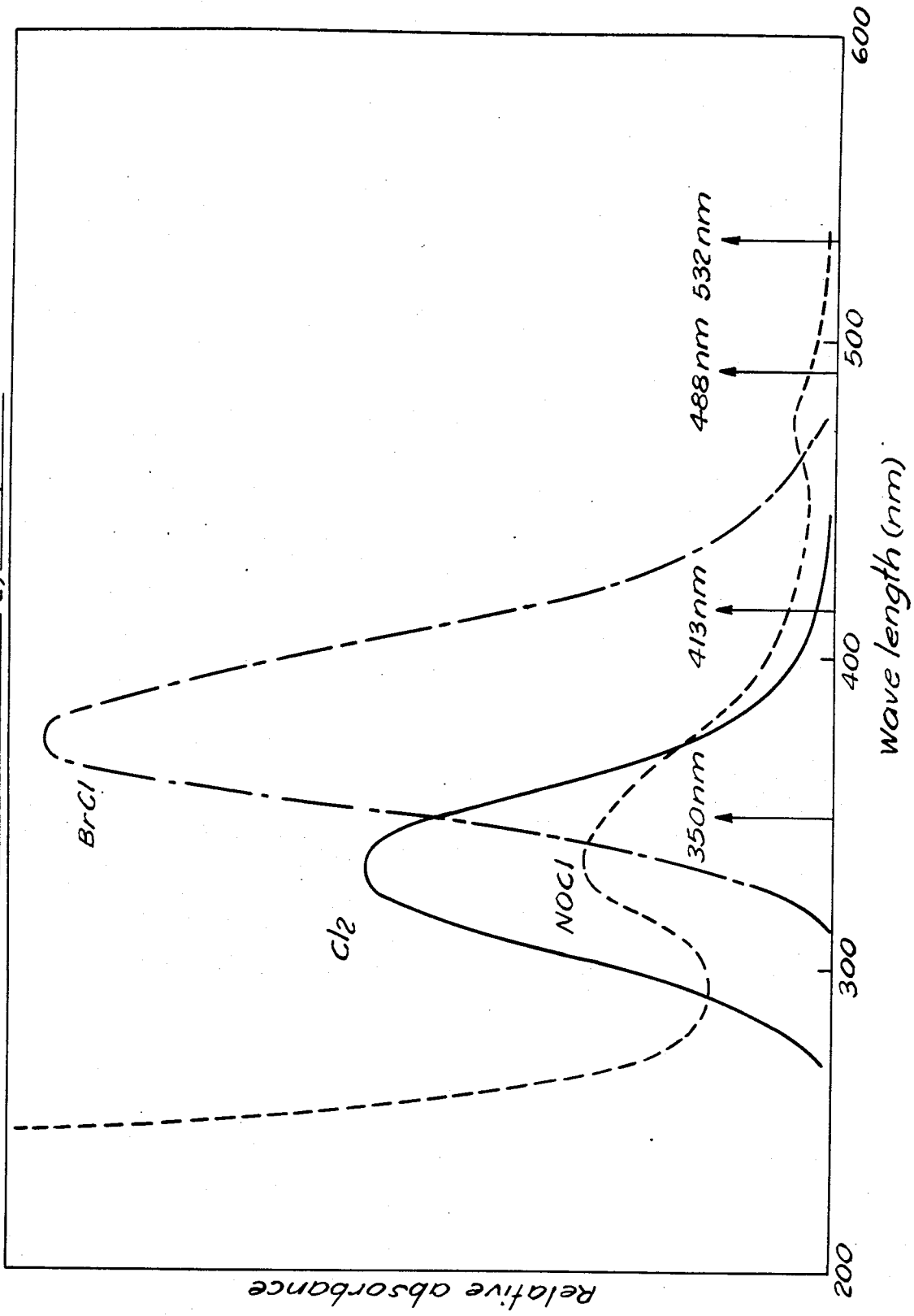

SELECTIVE PHOTOCHLORINATION OF 1,1-DICHLOROETHANE

CROSS-REFERENCE TO RELATED APPLICATION

This application is a continuation of copending application Ser. No. 499,088, filed May 27, 1983, now abandoned, which is a continuation-in-part of copending application Ser. No. 386,148, filed June 7, 1982, now abandoned.

BACKGROUND OF THE INVENTION

This invention relates to a process for producing 1,1,1-trichloroethane by reacting 1,1-dichloroethane with chlorine.

1,1,1-Trichloroethane is commonly produced by the hydrochlorination of vinylidene chloride or the chlorination of 1,1-dichloroethane. The latter has been done by either thermal chlorination or photochlorination. The photochlorination is presently done by irradiating mixtures of 1,1-dichloroethane and chlorine with broad spectrum lamps.

The major problem in such chlorination reactions is the production of by-products, mainly 1,1,2-trichloroethane. Other by-products produced include 1,1,2,2-tetrachloroethane, 1,1,1,2-tetrachloroethane and 1,1,1,2,2-pentachloroethane. In the conventional chlorination reactions, in excess of 30 percent of the 1,1-dichloroethane chlorinated forms these by-products. Mintz, U.S. Pat. No. 3,580,831, teaches that catalytic amounts of iodine improve the selectivity of photochlorination of mono- and 1,1-dichloroethane with actinic light.

In Okado et al., Japanese Pat. No. 55-079,329 (1980), the use of iodine and iodine compounds to improve the selectivity of chlorination of 1,1-dichloroethane is taught. It is further taught that the use of iodine or iodine compounds in liquid phase photochlorination results in especially good selectivity.

Okado et al., German Pat. No. 3,011,689, teaches the use of iodine and iodine compounds as catalysts in vapor phase photochlorination of 1,1-dichloroethane and that these catalysts improve selectivity.

Rideout et al., U.S. Pat. No. 4,301,314, teaches that the addition of between 100 and 600 parts per million of oxygen during the thermal chlorination of 1,1-dichloroethane improves the selectivity of that reaction for 1,1,1-trichloroethane. Rideout et al., U.S. Pat. No. 4,192,823, teaches that the addition of between about 500 to 100,000 parts per million of carbon dioxide during the thermal chlorination of 1,1-dichloroethane improves the selectivity of that reaction for 1,1,1-trichloroethane.

SUMMARY OF THE INVENTION

The invention is a selective process for preparing 1,1,1-trichloroethane comprising irradiating a vaporous mixture comprising 1,1-dichloroethane, chlorine and an effective amount of a photocatalyst wherein the photocatalyst is bromine, a compound which liberates bromine in the presence of chlorine, carbon monoxide, nitric oxide or oxygen, with radiation capable of inducing the selective formation of 1,1,1-trichloroethane. Radiation in the wavelength of between about 250 and 550 nanometers is capable of inducing the selective formation of 1,1,1-trichloroethane.

This process results in a reaction with surprisingly higher selectivity for 1,1,1-trichloroethane.

DESCRIPTION OF THE DRAWING

The FIGURE is a plot of relative absorption of $Cl_2$, BrCl and NOCl against wavelength.

DETAILED DESCRIPTION OF THE INVENTION

It has been discovered that certain photocatalysts significantly increase the selectivity of the photochlorination reaction of 1,1-dichloroethane with chlorine to produce 1,1,1-trichloroethane. Suitable photocatalysts are elements or compounds which readily react with chlorine to form binary compounds, called binary intermediates herein, which absorb light in the area between 250 and 550 nanometers. Suitable photocatalysts include bromine, a compound which liberates bromine in the presence of chlorine, nitric oxide, carbon monoxide and oxygen.

Any compound which liberates bromine in the presence of chlorine under the reaction conditions can be used in this invention. Examples of bromine-liberating compounds include hydrogen bromide; alkali metal bromides such as lithium bromide, sodium bromide, potassium bromide, rubidium bromide and cesium bromide; alkaline earth metal bromides such as beryllium bromide, magnesium bromide, barium bromide, calcium bromide and strontium bromide; organic bromides such as methyl bromide, ethyl bromide, propyl bromide, butyl bromide, methylene bromide, bromoform, ethylidene bromide, benzene bromide, benzene dibromide, toluene bromide and phenol bromide.

The term organic bromide includes aliphatic bromides, cycloaliphatic bromides and aromatic bromides. Aliphatic bromides include alkyl bromides, alkenyl bromides and alkynyl bromides. Aromatic bromides include all bromine compounds which contain an aryl group. The term aryl refers herein to biaryl, phenyl, naphthyl, phenanthranyl, anthranyl and two aryl groups bridged by an alkylene group. Alkyl includes straight- and branched-chain methyl, ethyl, propyl, butyl, pentyl, hexyl, heptyl, actyl, nonyl, decyl, undecyl, dodecyl, tridecyl, tetradecyl, pentadecyl, hexadecyl, heptadecyl, octadecyl, nonadecyl and eicosyl groups.

Preferable photocatalysts are bromine, hydrogen bromide, organic bromides, nitric oxide, carbon monoxide and oxygen. More preferred photocatalysts include bromine, hydrogen bromide, alkyl bromide, nitric oxide, carbon monoxide and oxygen. Even more preferred photocatalysts include bromine, oxygen, nitric oxide and carbon monoxide, with bromine most preferred.

When these photocatalysts are added to the 1,1-dichloroethane which is contacted with chlorine and then exposed to radiation of a wavelength which is absorbed by the binary intermediate, the selectivity of the reaction for 1,1,1-trichloroethane is significantly increased. It is preferable that the binary intermediate absorbs light of wavelengths different from those at which chlorine absorbs appreciably.

The above reaction is initiated by exposing the reactants and catalyst to radiation from a suitable source of light. Suitable sources of light include those which are capable of providing radiation in the wavelength between about 250 and 550 nanometers. It is preferable to use those light sources capable of providing monochromatic light, that is, radiation in a narrow wavelength band. Suitable light sources include lasers and mercury arc lamps fitted with appropriate filters. A monochromatic light source is preferred because the binary intermediate can be photo-excited without photo-exciting the chlorine present. It is believed that photo-excitation of chlorine increases the formation of by-products, whereas photo-excitation of the binary intermediate without photo-excitation of the chlorine results in formation of less by-products.

Suitable wavelengths of radiation capable of inducing the selective formation of 1,1,1-trichloroethane of this reaction are between about 250 and 550 nanometers. It is preferable to use light capable of providing radiation in the wavelength of 350–550 nanometers. The suitable wavelength for use with a certain binary intermediate formed depends upon where that binary intermediate absorbs. It is most preferable to use radiation at wavelengths between about 450 and 550 nanometers as chlorine does not absorb appreciably in this range. This reaction can be optimized by using monochromatic light which provides radiation at a wavelength at which the binary intermediate absorbs and chlorine does not appreciably absorb or has very low absorption. Very low absorption as used herein means that there is some noticeable absorption by chlorine at that wavelength but it is so low that there is very little photo-excitation of the chlorine and resultant by-product formation. "Does not absorb appreciably" as used herein means that there is no noticeable absorption by chlorine although there may actually be some negligible amount of absorption occurring. When bromine or a bromine-liberating compound is the photocatalyst, these optimum wavelengths are in a range between about 375 and 475 nanometers. When nitric oxide is the photocatalyst, these optimum wavelengths are in a range between about 400 to 500 nanometers. The FIGURE demonstrates those wavelengths at which the binary intermediates absorb and chlorine does not absorb appreciably or has very low absorption. It is shown that chlorine has very low absorption at the low end of the range of wavelengths including 375 to 475 nanometers and that the bromine chlorine binary intermediate has its highest absorption in this range. It is further shown that nitric oxide has its highest absorption in the wavelength range including 400 to 500 nanometers, and chlorine has very low absorption in the lower end of the range and does not absorb appreciably in the upper end. The FIGURE also shows chlorine does not absorb appreciably at a wavelength above 450 nanometers.

The photocatalyst is used in amounts in which the selectivity of the chlorination of 1,1-dichloroethane to 1,1,1-trichloroethane is increased.

Preferably the photocatalyst is employed in amounts which provide between about 50 and 5000 parts per million by weight of bromine, nitric oxide, oxygen or carbon monoxide based on 1,1-dichloroethane, more preferably between about 100 and 2500 parts per million and most preferably between about 500 and 1500 parts per million.

Between about 0.05 and 2.0 moles of chlorine per mole of dichloroethane can be used. It is preferable to use between 0.1 and 0.3 mole of chlorine per mole of 1,1-dichloroethane, as the selectivity of this reaction improves as the ratio of chlorine to 1,1-dichloroethane decreases. Further, if the ratio of chlorine to dichloroethane is too high, overchlorination takes place.

The process described herein is run at a temperature at which the reactants are in the vapor state. Suitable temperatures are between 50° C. and 400° C., preferably between about 80° C. and 150° C. The reactants are usually preheated to insure they are in the vapor phase before exposing them to the desired wavelengths of light.

The reaction may be run at subatmospheric, atmospheric and superatmospheric pressures provided the reactants are in the vapor state.

SPECIFIC EMBODIMENTS

The following examples are included for merely descriptive purposes and are not intended to limit the scope of the invention.

The mix of products prepared in the following examples is given by a ratio ($\alpha/\beta$) wherein $\alpha$ is the amount of 1,1,1-trichloroethane produced and $\beta$ is the amount of 1,1,2-trichloroethane.

EXAMPLE 1

1,1-Dichloroethane containing 1097 ppm $Br_2$ was pumped into a preheater at about 0.43 g/min. Chlorine gas was fed into the preheater at about 0.8 mmol/min. The reactants were pumped into a reactor after being preheated to 120° C. The reactor was irradiated with an argon ion laser set to deliver 2.0 watts at 488 nanometers. Gas chromatographic analysis of the product collected in the trap showed a 16 percent conversion of 1,1-dichloroethane and an $\alpha/\beta$ ratio of 8.9.

EXAMPLE 2

The photochemical reactor was the same as in Example 1. 1,1-Dichloroethane (0.43 g/min) (containing 1097 ppm $Br_2$) and $Cl_2$ (0.8 mmol/min) were fed into the preheater and preheated to 120° C. Thereafter the preheated mixture was passed into the reactor. The reactor was irradiated with a krypton ion laser set to deliver 2.0 watts at 350 nanometers. Gas chromatographic analysis of the product collected in the trap indicated a 19.4 percent conversion of 1,1-dichloroethane and an $\alpha/\beta$ ratio of 7.1.

EXAMPLE 3

The photochemical reactor was the same as in Example 1. 1,1-Dichloroethane (0.43 g/min) (containing 1097 ppm $Br_2$) and $Cl_2$ (0.8 mmol/min) were fed into the preheater and preheated to 120° C. Thereafter the mixture was irradiated in the reactor using a krypton ion laser set to deliver 2.0 watts at 413 nanometers. Gas chromatographic analysis of the product collected in the trap indicated a 20.7 percent conversion of 1,1-dichloroethane and an $\alpha/\beta$ ratio of 7.3.

EXAMPLE 4

A series of experiments similar to Example 1 were run, wherein different wavelengths and additives were used. Table I demonstrates the changes made and the $\alpha/\beta$ ratios achieved.

TABLE I

| 1,1,1-Trichloroethane/1,1,2-trichloroethane Ratio as a Function of Reaction Conditions | | | | |
|---|---|---|---|---|
| Wavelength (Nanometers) | Laser Type | Power (Watts) | Additive | $\alpha/\beta$ |
| 350 | Cont. | 2.0 | None[1] | 6.1 |
| 350 | Cont. | 2.0 | $I_2$ | 5.9 |
| 350 | Cont. | 2.0 | NO | 5.9 |
| 350 | Cont. | 2.0 | $Br_2$ | 7.1[2] |
| 413 | Cont. | 2.0 | $I_2$ | 8.2 |
| 413 | Cont. | 2.0 | $Br_2$ | 7.3[3] |

TABLE I-continued

| 1,1,1-Trichloroethane/1,1,2-trichloroethane Ratio as a Function of Reaction Conditions | | | | |
|---|---|---|---|---|
| Wavelength (Nanometers) | Laser Type | Power (Watts) | Additive | α/β |
| 488 | Cont. | 2.0 | None | 7.1 |
| 488 | Cont. | 2.0 | $I_2$ | 8.6 |
| 488 | Cont. | 2.0 | NO | 7.7 |
| 488 | Cont. | 2.0 | $Br_2$ | 8.9[4] |
| 514 | Cont. | 2.0 | None | 6.8 |

[1] None is equivalent to 50-100 parts per million of $Br_2$
[2] Example 2
[3] Example 3
[4] Example 1

All the above reactions were run at 120° C., 45 seconds contact time and ~5/1 α-Di/$Cl_2$.

What is claimed is:

1. A selective process for preparing 1,1,1-trichloroethane comprising irradiating a vaporous mixture comprising 1,1-dichloroethane, chlorine and an effective amount of a photocatalyst wherein the photocatalyst is bromine or a compound which liberates bromine in the presence of chlorine, with radiation capable of inducing the selective formation of 1,1,1-trichloroethane wherein the photocatalyst concentration is between about 500 and 5000 parts per million based on the weight of the 1,1-dichloroethane under conditions such that the ratio of 1,1,1-trichloroethane prepared to 1,1,2-trichloroethane prepared is about 7.1 or greater.

2. The process of claim 1 wherein an effective amount of the photocatalyst is that which provides between about 500 to 1500 parts of bromine per million by weight of the 1,1-dichloroethane.

3. The process of claim 1 wherein the photocatalyst is bromine, hydrogen bromide, an alkali metal bromide, an alkaline earth metal bromide or an organic bromide.

4. The process of claim 1 wherein the photocatalyst is bromine, hydrogen bromide or an organic bromide.

5. The process of claim 1 wherein the photocatalyst is bromine, hydrogen bromide or an alkyl bromide.

6. The process of claim 1 wherein the radiation capable of inducing the selective formation of 1,1,1-trichloroethane has a wavelength between about 250 and 550 nanometers.

7. The process of claim 1 wherein the radiation is provided by a monochromatic light source.

8. The process of claim 1 wherein the radiation has a wavelength of between about 350 and 550 nanometers.

9. The process of claim 1 wherein the radiation has a wavelength of between about 450 and 550 nanometers.

10. The process of claim 1 wherein the amount of chlorine contacted with the 1,1-dichloroethane is between about 0.05 and 2.0 moles of chlorine per mole of 1,1-dichloroethane.

11. The process of claim 10 wherein the amount of chlorine contacted with the 1,1-dichloroethane is between about 0.1 and 0.3 mole of chlorine per mole of 1,1-dichloroethane.

12. The process of claim 1 wherein the photocatalyst is bromine or a compound which liberates bromine in the presence of chlorine and the radiation is of a wavelength between about 375 and 475 nanometers.

13. A selective process for preparing 1,1,1-trichloroethane comprising irradiating a vaporous mixture comprising 1,1-dichloroethane, chlorine and an effective amount of a photocatalyst selected from the group consisting of bromine or a compound which liberates bromine in the presence of chlorine, with radiation capable of inducing the selective formation of 1,1,1-trichloroethane under conditions such that the ratio of 1,1,1-trichloroethane to 1,1,2-trichloroethane is 7.1 or greater wherein the photocatalyst concentration is between about 500 and 5000 parts per million based on the weight of 1,1-dichloroethane.

14. The process of claim 13 wherein the ratio of 1,1,1-trichloroethane to 1,1,2-trichloroethane is 8.0 or greater.

* * * * *